United States Patent [19]

Inabinet et al.

[11] Patent Number: 5,281,733
[45] Date of Patent: Jan. 25, 1994

[54] PROCESS FOR PRODUCING MMT

[75] Inventors: Carl O. Inabinet, St. Matthews; Fred H. Gregory, Orangeburg, both of S.C.; David M. Marchand, Baton Rouge, La.; Robert B. Agee, Orangeburg, S.C.

[73] Assignee: Ethyl Corporation, Richmond, Va.

[21] Appl. No.: 893,951

[22] Filed: Jun. 4, 1992

Related U.S. Application Data

[63] Continuation of Ser. No. 710,400, Jun. 5, 1991, abandoned.

[51] Int. Cl.$^5$ .............. C07F 13/00; C07F 17/00; C07F 11/00
[52] U.S. Cl. .................. 556/47; 556/43; 556/53; 556/60; 556/112; 556/121; 556/136; 556/144
[58] Field of Search ............. 556/47, 43, 53, 60, 556/112, 121, 136, 144

[56] References Cited

U.S. PATENT DOCUMENTS

| | | | |
|---|---|---|---|
| 2,818,416 | 12/1957 | Brown et al. | 260/429 |
| 2,818,417 | 12/1957 | Brown et al. | 260/429 |
| 2,839,552 | 6/1958 | Shapiro et al. | 260/429 |
| 2,868,816 | 1/1959 | Petree | 260/429 |
| 2,915,440 | 12/1959 | Pearson | 204/59 |
| 2,915,539 | 12/1959 | Bergeron et al. | 556/47 |
| 2,916,504 | 12/1959 | Shapiro | 260/429 |
| 2,916,505 | 12/1959 | Shapiro | 260/429 |
| 2,960,514 | 11/1960 | Brown et al. | 260/429 |
| 2,964,547 | 12/1960 | De Witt et al. | 260/429 |
| 2,987,528 | 6/1961 | Brown et al. | 260/429 |
| 2,987,529 | 6/1961 | Sims | 260/429 |
| 2,987,530 | 6/1961 | Pearson et al. | 260/429 |
| 2,987,531 | 6/1961 | Shapiro et al. | 260/429 |
| 3,040,077 | 6/1962 | Freeman, Jr. | 556/47 |
| 3,041,155 | 6/1962 | Brown et al. | 44/69 |
| 4,946,975 | 8/1990 | Wu et al. | 556/47 |
| 5,026,885 | 6/1991 | Bell et al. | 556/47 |

FOREIGN PATENT DOCUMENTS 0921031  3/1963  United Kingdom .................. 556/47

Primary Examiner—Paul F. Shaver
Assistant Examiner—Porfirio Nazario
Attorney, Agent, or Firm—Richard J. Hammond

[57] ABSTRACT

A process for the carbonylation of substituted metal coordination compounds in the presence of carbon monoxide at a pressure in excess of 400 psig to produce optionally substituted cyclopentadienyl metallic carbonyls, particularly methylcyclopentadienyl manganese tricarbonyl in a thin-film-producing reactor.

16 Claims, No Drawings

PROCESS FOR PRODUCING MMT

This is a continuation of copending application Ser. No. 07/710,400 filed on Jun. 5, 1991, now abandoned.

FIELD OF INVENTION

This invention relates to the production of organometallic compounds and more specifically to a process for the production of substituted cyclopentadienyl metal coordination compounds of certain specified types.

Organometallic compounds which contain a cyclopentadienyl radical and some other electron donating group coordinated with a metal radical have been shown to have beneficial qualities as additives in liquid hydrocarbons. However, it has become desirable to develop methods of production that increase the amount of such substituted cyclopentadienyl metal coordination compounds yielded and methods that increase the rate of said production.

BACKGROUND OF INVENTION

U.S. Pat. No. 3,178,463 discloses the formation of compounds of iron, ruthenium and osmium in which three carbonyl groups and a compound containing a cyclopentadiene configuration are bonded to the metal atom. Said compounds are depicted by the empirical formula $C_yHM(CO)_3$, wherein $C_yH$ is a cyclopentadiene hydrocarbon and M is an iron subgroup metal, i.e., iron, ruthenium or osmium.

U.S. Pat. No. 4,674,447 discloses improvements in the operation of gasoline internal combustion engines in which the gasoline contains an organic manganese compound.

U.S. Pat. No. 4,946,975 discloses a process for making methylcyclopentadienyl manganese tricarbonyl compounds. The process disclosed involves forming a mixture of bis(methylcyclopentadienyl) manganese and manganese acetate, reacting this mixture with an alkyl aluminum compound in the presence of an ether donor compound in an amount to provide about 1 mole of ether per mole of aluminum alkyl and reacting the resultant product with carbon monoxide to produce methylcyclopentadienyl manganese tricarbonyl.

OBJECTS OF THE INVENTION

It is an object of this invention to provide a process for increasing yields in the carbonylation of substituted cyclopentadienyl metal coordination compounds to produce substituted cyclopentadienyl metal coordination carbonyls.

Another object of this invention is to provide a process for increasing the rate of reaction in the carbonylation of substituted cyclopentadienyl metal coordination compounds.

The above and other objects of this invention are met by providing a process for the production of a process for producing a compound of the formula $R_xAMB_yC_z$ where R is an alkyl, substituted alkyl, aryl, aralkyl, acyl or alkenyl group from $C_1$–$C_6$, x is a small integer from 1 to 2, A is an organic cyclopentadienyl radical, M is a transition metal, B and C are electron donating groups different from a cyclopentadienyl radical, y is a small integer from 1 to 4 inclusive and z is a small integer from 0 to 2 inclusive such that the metal atom is in a state of maximum covalence.

PREFERRED EMBODIMENTS OF THE INVENTION

Thus, the process of this invention comprises the production of a compound having a formula $R_xAMB_yC_z$ where A is a substituted cyclopentadienyl radical having as substituents one or more alkyl, substituted alkyl, aryl aralkyl, acyl or alkenyl groups R, M, C, x, y and z as defined hereinabove.

The transition metal, M, in the above formula comprises metals from groups IVB, VB, VIB, VIIB, VIII, IB, and IIB of the periodic table, namely the elements titanium, vanadium, chromium, molybdenum, tungsten, manganese, rhenium, iron, cobalt, nickel, copper and zinc. Of these metals, those of group VIIB are preferred. Manganese is particularly preferred as such compounds containing manganese have been found to have desirable anti-knock qualities when added to hydrocarbon fuels.

The cyclopentadienyl radical, A, in the above formula can be represented as a cyclomatic hydrocarbon by the general formula:

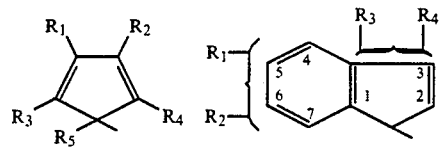

where the R's are selected from the group consisting of hydrogen and univalent organic hydrocarbon radicals. Those cyclopentadienyl radicals having up to 13 carbon atoms are preferred. The methylcyclopentadienyl radical is particularly preferred as it has shown useful in the formation of anti-knock compounds.

The groups represented by B and C in the formula shown above are designated as electron donating groups other than a cyclopentadienyl containing radical. Electron donating groups, generally, are groups which are capable of sharing electrons with a metal atom such that the metal atom achieves a noble gas structure due to the donated electrons of the electron donating groups and the cyclopentadienyl group. These electron donating groups are either radicals or molecular species with unstable electrons, which electrons assume a more stable configuration in the molecules when associated with a metal to give the metal's outer electron shell the configuration of a noble gas. Hydrogen, the cyano group, and the isonitrile radical are examples of electron donors which donate a single electron, while carbon monoxide, ammonia and primary, secondary, and tertiary amines are examples of donor groups which donate two electrons. An example of a three electron donor is the nitrosyl group. The carbonyl group, CO, is a preferred constituent of the process of this invention as it has been found to be particularly useful in the formation of compounds which function as anti-knock agents in liquid hydrocarbon fuels.

Therefore, an embodiment of this invention comprises the carbonylation of a group VIIB transition metal coordination compound containing a cyclopentadienyl radical having up to 13 carbon atoms.

A preferred embodiment of this invention is the carbonylation of said compounds in which the group VIIB transition metal, M, is manganese. It has been found that compounds having the formula $AMn(CO)_3$ are superior anti-knock agents when added to liquid hydrocarbon fuels which are used in the operation of spark ignition internal combustion engines.

The process of this invention is preferably carried out in a suitable solvent which is inert and remains in a liquid state under the conditions of this invention's reaction. Nitrobenzene and petroleum ethers are examples of such solvents.

Another preferred embodiment of this invention comprises conducting the carbonylation of the cyclopentadienyl metal coordination compounds in a thin-film-producing reactor.

A further preferred embodiment of this invention comprises conducting the carbonylation of the cyclopentadienyl metal coordination compounds in a vertical packed bed reactor.

The use of vertical packed bed reactors is fully illustrated in the prior art. Examples of such may be seen in the *Chemical Engineers' Handbook*, Fourth Edition, by John H. Perry, pages 18-25 and following, and the *Kirk-Othmer Encyclopedia of Chemical Technology*, Third Edition, Volume 7, page 878 and following, both of which are incorporated herein in toto by reference.

Said vertical packed bed reactors have been found to be advantageous due to increased surface area contact between the cyclopentadienyl metal coordination compounds and the carbon monoxide gas involved in a preferred embodiment of the present invention. In order to accomplish increased surface area contact between the reactants the vertical packed bed reactor column may be packed with various packing materials. Packing materials such as beads, pellets, wire mesh, etc., may be used. In addition, commercially available packing materials such as screens, pall rings, Raschig rings, Lessing rings, tellerettes, Berl saddles, Koch Flexipac packing, Intalox saddles, etc., may be utilized to divert liquid and gas flow in the reactor.

The reaction between the liquid and gaseous reactants in the present invention is conducted at a pressure in excess of 400 psig, with the upper limits of reaction pressure being the limitations of the particular apparatus used. The reaction is conducted at a temperature in the range of between about 160° C. and about 240° C. Ordinarily, the reaction is conducted at temperature of about 200° C. Reactants are preferably allowed to mix at the reaction temperature. The reactants may be preheated prior to introduction to the thin-film-producing reactor and insulating and heating equipment may be utilized to maintain a desirable reaction temperature along the length of the reactor. Reaction times will vary depending upon the variable reaction conditions such as reaction temperature and pressure, flow rate of reactants and the amount of recirculation of reactants utilized.

The following examples are illustrative of the present invention:

COMPARATIVE EXAMPLE

A current process for the production of methylcyclopentadienyl manganese tricarbonyl (MMT) consists of a single batch process, such as demonstrated as follows:

Into a reaction flash under nitrogen was placed 1.26 parts bis(methylcyclopentadienyl) manganese (91.8% pure), 0.93 parts manganous acetate, 0.78 parts tetrahydrofuran (THF) and 17.31 parts toluene. Over a period of 15 minutes, a solution of 1.24 parts triethyl aluminum (TEA) in 8.70 parts toluene was added to the above mixture with a vigorous stirring (Al:Mn atom ratio 1:1, TEA:THF mole ratio 1:1). The solution darkened slightly. This solution of the intermediate complex was transferred under nitrogen to stainless steel autoclave. The autoclave was sealed, pressurized twice to 300 psig with carbon monoxide and vented and finally pressurized with carbon monoxide to 600 psig and heated while stirring at 100° C. Carbon monoxide was added as needed to maintain 600 psig. After two hours at 100° C., the temperature Was raised to 150° C. for 30 minutes. The autoclave was then cooled, vented and discharged. The mixture was hydrolyzed with 10% aqueous HCl. An equal volume of pentane was added to extract the MMT. The pentane phase was analyzed by gas chromatograph (GC) using a pentadecane internal standard to show a yield of MMT based on manganese of 84% and, based on MCP, of 89%.

EXAMPLES

As an example of the current invention, a packed bed reactor has been utilized in the production of methylcyclopentadienyl manganese tricarbonyl. In each of the following examples, the packed bed reactor consisted of a 69 inch long, schedule 160, two-inch pipe. A four inch spherical bulb was placed above the feed point to provide for vapor disentrainment. The tube was packed with Koch Flexipac stainless steel packing. Externally, the tube was wrapped with copper coils and insulated. Thermocouples were then utilized to maintain a desired reaction temperature through the length of the tube. A reaction mixture containing a 43% $R_2Mn$ solution was fed into the top of the packed bed reactor. Gaseous carbon monoxide was fed under pressure control though a side tube and liquid level was maintained by removing the product through a differential pressure transmitter with a port at the bottom of the reactor. Gaseous inerts were vented from the top of the reactor through a wet test meter.

As indicated by the following table, the percentage yield of the continuous carbonylation process is less than that for the single batch method. A benefit of the continuous carbonylation method is that the increased rate of reaction corresponds to an overall increase in the amount of the desired product.

| Run | 1 | 2 | 3 |
|---|---|---|---|
| Rate (Grams/min.) | 25.6 | 25.6 | 25.6 |
| Pressure (psi) | 600 | 600 | 600 |
| Temp. (°C.) | | | |
| top | 100 | 125 | 132 |
| middle | 182 | 183 | 157 |
| bottom | 184 | 185 | 168 |
| average* | 183 | 184 | 163 |
| % Yield | 52.9 | 59.0 | 59.5 |

*Middle and bottom temperatures.

What is claimed:

1. In a process for the carbonylation of substituted cyclopentadienyl metal coordination compounds in the presence of carbon monoxide to produce a mixture containing optionally substituted alkyl cyclopentadienyl metallic carbonyls and unreacted substituted cyclopentadienyl metal coordination compounds, wherein the improvement comprises conducting said carbonylation reaction in a thin-film-producing reactor.

2. The process of claim 1 in which the thin-film-producing reactor is a vertical packed bed reactor.

3. The process of claim 1 in which the reaction is conducted at a pressure of between about 400 psig and about 2,000 psig.

4. The process of claim 1 in which the reaction is conducted at a pressure of between about 500 psig and about 900 psig.

5. The process of claim 1 in which the reaction is conducted at a pressure of between about 600 psig and about 800 psig.

6. The process of claim 1 in which the reaction is conducted at a temperature of between about 160° C. and about 240° C.

7. The process of claim 1 in which the reaction is conducted at a temperature of between about 175° C. and about 225° C.

8. The process of claim 1 in which the reaction is conducted at a temperature of between about 190° C. and about 210° C.

9. The process of claim 1 in which the substituted cyclopentadienyl metal coordination compounds contain metals from groups VIIB and VIII.

10. The process of claim 1 in which the substituted cyclopentadienyl metal coordination compounds are manganese bismethyl cyclopentadienes.

11. The process of claim 1 in which the substituted cyclopentadienyl metal coordination compounds are manganese methyl cyclopentadienes.

12. The process of claim 1 in which the resulting mixture of unreacted substituted cyclopentadienyl metal coordination compounds and optionally substituted cyclopentadienyl metallic carbonyls is recirculated in the presence of carbon monoxide through said thin-film-producing reactor.

13. The process of claim 1 in which the resulting mixture of unreacted cyclopentadienyl metal coordination compounds and optionally substituted cyclopentadienyl metallic carbonyls is recirculated in the presence of carbon monoxide through said thin-film-producing reactor until the percent yield of optionally substituted cyclopentadienyl metallic carbonyls is equal to or greater than 70%.

14. The process of claim 2 in which the vertical packed bed reactor contains glass beads as a packing material.

15. The process of claim 2 in which the resulting mixture of unreacted substituted cyclopentadienyl metal coordination compounds and optionally substituted cyclopentadienyl metallic carbonyls is recirculated in the presence of carbon monoxide through said thin-film-producing reactor.

16. The process of claim 2 in which the resulting mixture of unreacted cyclopentadienyl metal coordination compounds and optionally substituted cyclopentadienyl metallic carbonyls is recirculated in the presence of carbon monoxide through said thin-film-producing reactor until the percent yield of optionally substituted cyclopentadienyl metallic carbonyls is equal to or greater than 70%.

* * * * *